US009000139B2

(12) United States Patent
Sung et al.

(10) Patent No.: US 9,000,139 B2
(45) Date of Patent: Apr. 7, 2015

(54) COMPOSITION FOR PREVENTING OR TREATING CERVICAL CANCER HAVING HUMAN PAPILLOMAVIRUS PLASMODIUM AND IMMUNITY ENHANCER

(75) Inventors: Young Chul Sung, Gyeongsangbuk-do (KR); Sang Hwan Seo, Gyeongsangbuk-do (KR); You Suk Suh, Seoul (KR)

(73) Assignee: Genexine, Inc., Gyeonggi-Do (KR)

( * ) Notice: Subject to any disclaimer, the term of this patent is extended or adjusted under 35 U.S.C. 154(b) by 0 days.

(21) Appl. No.: 13/816,716

(22) PCT Filed: Aug. 13, 2010

(86) PCT No.: PCT/KR2010/005367
§ 371 (c)(1),
(2), (4) Date: Mar. 20, 2013

(87) PCT Pub. No.: WO2012/020871
PCT Pub. Date: Feb. 16, 2012

(65) Prior Publication Data
US 2013/0195905 A1 Aug. 1, 2013

(51) Int. Cl.
*C07K 14/01* (2006.01)
*C12N 15/62* (2006.01)
*C07K 14/005* (2006.01)

(52) U.S. Cl.
CPC ............. *C07K 14/01* (2013.01); *C07K 2319/00* (2013.01); *C07K 2319/036* (2013.01); *C12N 15/62* (2013.01); *C12N 2710/20034* (2013.01); *C12N 2710/20022* (2013.01); *C07K 14/005* (2013.01)

(58) Field of Classification Search
None
See application file for complete search history.

(56) References Cited

U.S. PATENT DOCUMENTS

| 6,004,557 A | 12/1999 | Edwards et al. |
| 6,342,224 B1 | 1/2002 | Bruck et al. |
| 8,137,674 B2 | 3/2012 | Sung et al. |

FOREIGN PATENT DOCUMENTS

| CN | 1679930 A | 10/2005 |
| EP | 1 243 655 A1 | 9/2002 |
| EP | 1 757 615 A1 | 2/2007 |
| JP | 10-510989 A | 10/1998 |
| JP | 2001-513986 A | 9/2001 |
| JP | 2009-534027 A | 9/2009 |
| KR | 10 19980009278 A | 4/1998 |
| KR | 10 2003 0047667 B1 | 6/2003 |
| KR | 10 2005 0053732 A | 6/2005 |
| KR | 10 20090007333 A | 1/2009 |
| WO | WO 96/19496 A1 | 6/1996 |
| WO | WO 01/19408 A1 | 3/2001 |
| WO | WO 2004/030636 A2 | 4/2004 |
| WO | WO 2007/119896 A1 | 10/2007 |
| WO | WO 2009/106362 A1 | 9/2009 |

OTHER PUBLICATIONS

Seo et al. Optimal induction of HPV DNA vaccine-induced CD8+ T cell responses and therapeutic antitumor effect by antigen engineering and electroporation. Vaccine. Sep. 25, 2009;27(42):5906-12. doi: 10.1016/j.vaccine.2009.07.033. Epub Aug. 3, 2009.*
Borysiewicz et al. A recombinant vaccinia virus encoding human papillomavirus types 16 and 18, E6 and E7 proteins as immunotherapy for cervical cancer. Lancet. Jun. 1, 1996;347(9014):1523-7.*
FLT3LG protein [*Homo sapiens*] GenBank: AAI44130.1. Dated Jan. 8, 2009. http://www.ncbi.nlm.nih.gov/protein/219841754?report=genbank&log$=protalign&blast_rank=1& RID=PR3T8RYN014.*
Lethal factor domain I [synthetic construct] GenBank: AAR88323.1. Dated Sep. 15, 2004. http://www.ncbi.nlm.nih.gov/protein/40646957?report=genbank&log$=protalign&blast_rank=4&RID=PR48H4KU014.*
E6 [Human papillomavirus type 16]. GenBank: AAD33252.1. Dated Jun. 30, 2000. http://www.ncbi.nlm.nih.gov/protein/AAD33252.1.*
E7 [Human papillomavirus type 16]. GenBank: AAD33253.1. Dated Jun. 30, 2000. http://www.ncbi.nlm.nih.gov/protein/AAD33253.1.*
Human papillomavirus type 18 E6, E7, E1, E2, E4, E5, L1 & L2 genes. GenBank: X05015.1. Dated Apr. 18, 2005. http://www.ncbi.nlm.nih.gov/nuccore/60975.*
Dochez et al. HPV vaccines to prevent cervical cancer and genital warts: an update. Vaccine. Mar. 20, 2014;32(14):1595-601.*
Bourgault Villada, I., et al., "Identification in humans of HPV-16 E6 and E7 protein epitopes recognized by cytolytic T lymphocytes in association with HLA-B18 and determination of the HLA-B18-specific binding motif," European Journal of Immunology 30(8):2281-2289, Wiley-VCH, Germany (2000).
Chen, H.-W., et al., "Identification of HLA-A11-restricted CTL epitopes derived from HPV type 18 using DNA immunization," Cancer Biology & Therapy 8(21):2025-2032, Taylor & Francis, United States (2009).
Facchinetti, V., et al., "CD4+ T cell immunity against the human papillomavirus-18 E6 transforming protein in healthy donors: identification of promiscuous naturally processed epitopes," European Journal of Immunology 35(3):806-815, Wiley-VCH, Germany (2005).

(Continued)

*Primary Examiner* — Louise Humphrey
(74) *Attorney, Agent, or Firm* — Sterne, Kessler, Goldstein & Fox P.L.L.C.

(57) ABSTRACT

A composition for preventing or treating cervical cancer comprising a human papillomavirus plasmodium and an immunity enhancer is provided. A fusion protein including a fusion polypeptide recombined to transform a 3D structure of E6 and E7, which are antigens against types 16 and 18 human papillomavirus (HPV), a signal peptide for secreting the fusion polypeptide outside the cells and an immunity enhancer peptide present in an individual is also provided. The fusion protein may be useful in treating HPV-triggered tumors by inducing an immune response specific to the antigens against the HPV types 16 and 18.

25 Claims, 3 Drawing Sheets

(56) References Cited

OTHER PUBLICATIONS

Gallagher, K.M.E. and Man, S., "Identification of HLA-DR1- and HLA-DR15-restricted human papillomavirus type 16 (HPV16) and HPV18 E6 epitopes recognized by CD4+ T cells from healthy young women," The Journal of General Virology 88(Pt 5):1470-1478, Society for General Microbiology, England (2007).

Kather, A., et al., "Identification of a Naturally Processed HLA-A 0201 HPV18 E7 T Cell Epitope by Tumor Cell Mediated in Vitro Vaccination," International Journal of Cancer 104(3):345-353, Wiley-Liss, United States (2003).

Morishima, S., et al., "Identification of HLA-A24-restricted cytotoxic T lymphocyte epitope from human papillomavirus type-16 E6: the combined effects of bortezomib and interferon-gamma on the presentation of a cryptic epitope," International Journal of Cancer 120(3):594-604, Wiley-Liss, United States (2006).

Nakagawa, M., et al., "Different Methods of Identifying New Antigenic Epitopes of Human Papillomavirus Type 16 E6 and E7 Proteins," Clinical and Diagnostic Laboratory Immunology 11(5):889-896, Amercican Society for Microbiology, United States (2004).

Nakagawa, M., et al. "HLA class I Binding Promiscuity of the CD8 T-cell Epitopes of Human Papillomavirus Type 16 E6 Protein," Journal of Virology 81(3):1412-1423, American Society for Microbiology, United States (2007).

Peng, S., et al., "Development of a DNA Vaccine Targeting Human Papillomavirus Type 16 Oncoprotein E6," Journal of Virology 78(16):8468-8476, American Society for Microbiology, United States (2004).

Ressing, M.E., et al., "Human CTL Epitopes Encoded by Human Papillomavirus Type 16 E6 and E7 Identified Through in Vivo and in Vitro Immunogenicity Studies of HLA-A 0201-binding peptides," The Journal of Immunology 154(11)5934-5943, American Association of Immunologists, United States (1995).

Ressing, M.E., et al., "Occasional Memory Cytotoxic T-Cell Responses of Patients with Human Papillomavirus Type 16-Positive Cervical Lesions Against a Human Leukocyte Antigen-A 0201-Restricted E7-Encoded Epitope," Cancer Research 56(3):582-588, American Association for Cancer Research, United States (1996).

Rudolf, M.P., et al., "Human T-Cell Responses to HLA-A-restricted High Binding Affinity Peptides of Human Papillomavirus Type 18 Proteins E6 and E7," Clinical Cancer Research 7(3 Suppl):788s-795s, American Association of Cancer, United States (2001).

Stauss, H.J., et al., "Induction of cytotoxic T lymphocytes with peptides in vitro: Identification of canidate T-cell epitopes in human papilloma virus," Proceedings of the National Academy of Sciences of the United States of America 89(17):7871-7875, National Academy of Sciences, United States (1992).

Yan, J., et al., "Cellular immunity induced by a novel HPV18 DNA vaccine encoding an E6/E7 fusion consensus protein in mice and rhesus macaques," Vaccine 26(40):5210-5215, Elsevier Science, Netherlands (2008).

Cobrinik, D. et al., "The retinoblastoma protein and the regulation of cell cycling," TIBS 17:312-315, Elsevier Science Publishers, England (1992).

Garcia, F., et al., "ZYC101a for Treatment of High-Grade Cervical Intraepithelial Neoplasia: A Randomized Controlled Trial," Obstetrics and Gynecology 103(2):317-326, Lippincott Williams & Wilkins, United States (2004).

Öhlschläger P., et al., "An improved rearranged Human Papillomavirus Type 16 E7 DNA vaccine candidate (HPV-16 E7SH) induces an E7 wildtype-specific T cell response," Vaccine 24:2880-2893, Elsevier Ltd., England (2006).

Schiffman, M.H., et al., "Epidemiologic Evidence Showing That Human Papillomavirus Infection Causes Most Cervical Intraepithelial Neoplasia," Journal of the National Cancer Institute 85(12):958-964, National institutes of Health, united States (1993).

Von Knebel Doeberitz, M., et al., "Inhibition of tumorigenicity of cervical cancer cells in nude mice by HPV E6-E7 anti-sense RNA," Int. J. Cancer 51:831-834, Wiley-Liss, Inc., United States (1992).

Yan, J., et al., "Induction of antitumor immunity in vivo following delivery of a novel HPV-16 DNA vaccine encoding an E6/E7 fusion antigen," Vaccine 27:431-440, Elsevier Ltd., England (2009).

Zur Hausen, H., "Papillomavirus infections—a major cause of human cancers," Biochimica et Biophysica Acta 1288:F55-F78, Elsevier Science B.V., Netherlands (1996).

Acession No. ACI43214.1, NCBI Database, accessed at http://ncbi.nlm.nih.gov/protein/ACI43214.1, accessed on Oct. 7, 2014.

Borysiewicz L.K., et al., "A recombinant vaccinia virus encoding human papillomavirus types 16 and 18, E6 and E7 proteins as immunotherapy for cervical cancer," The Lancet 347:1523-1527, Lancet Pub. Group, England (1996).

Seo, S.H., et al., "Optimal induction of HPV DNA vaccine-induced CD8[30] T cell responses and therapeutic antitumor effect by antigen engineering and eletroporation," Vaccine 27:5906-5912, Elsevier Ltd., England (Aug. 3, 2009).

English Language Abstract of Chinese Patent Publication No. CN 1679930 A, Chinese Patent Office, espacenet database (2005) (listed as document FP14 on the accompanying form PTO/SB/08A).

* cited by examiner

SEQUENCE LISTING

<160> NUMBER OF SEQ ID NOS: 6

<210> SEQ ID NO 1
<211> LENGTH: 579
<212> TYPE: PRT
<213> ORGANISM: Artificial Sequence
<220> FEATURE:
<223> OTHER INFORMATION: Structurally modified E6 and E7 derived from
      HPV16 and HPV18

<400> SEQUENCE: 1

Met His Gln Lys Arg Thr Ala Met Phe Gln Asp Pro Gln Glu Arg Pro
1               5                   10                  15

Arg Lys Leu Pro His Leu Cys Thr Glu Leu Gln Thr Thr Ile His Asp
                20                  25                  30

Ile Ile Leu Glu Cys Val Tyr Cys Lys Gln Gln Leu Leu Arg Arg Glu
            35                  40                  45

```
Val Tyr Asp Phe Ala Phe Arg Asp Leu Cys Ile Val Tyr Arg Asp Gly
     50                  55                  60

Asn Pro Tyr Ala Val Cys Asp Lys Cys Leu Lys Phe Tyr Ser Lys Ile
 65                  70                  75                  80

Ser Glu Tyr Arg Tyr Met His Gly Asp Thr Pro Thr Leu His Glu Tyr
                 85                  90                  95

Met Leu Asp Leu Gln Pro Glu Thr Thr Asp Leu Tyr Cys Tyr Glu Gln
            100                 105                 110

Leu Asn Asp Ser Ser Glu Glu Glu Asp Glu Ile Asp Gly Pro Ala Gly
                115                 120                 125

Gln Ala Glu Pro Asp Arg Ala His Tyr Asn Ile Val Thr Phe Cys Cys
            130                 135                 140

Lys Cys Asp Ser Thr Leu Asp Lys Cys Leu Lys Phe Tyr Ser Lys Ile
145                 150                 155                 160

Ser Glu Tyr Arg Tyr Tyr Cys Tyr Ser Val Tyr Gly Thr Thr Leu Glu
                165                 170                 175

Gln Gln Tyr Asn Lys Pro Leu Cys Asp Leu Leu Ile Arg Cys Ile Asn
                180                 185                 190

Cys Gln Lys Pro Leu Cys Pro Glu Glu Lys Gln Arg His Leu Asp Lys
            195                 200                 205

Lys Gln Arg Phe His Asn Ile Arg Gly Arg Trp Thr Gly Arg Cys Met
            210                 215                 220

Ser Cys Cys Arg Ser Ser Arg Thr Arg Arg Glu Thr Gln Leu His Tyr
225                 230                 235                 240

Asn Ile Val Thr Phe Cys Cys Lys Cys Asp Ser Thr Leu Arg Leu Cys
                245                 250                 255

Val Gln Ser Thr His Val Asp Ile Arg Thr Leu Glu Asp Leu Leu Met
            260                 265                 270

Gly Thr Leu Gly Ile Val Cys Pro Ile Cys Ser Gln Lys Pro Met Ala
            275                 280                 285

Arg Phe Glu Asp Pro Thr Arg Arg Pro Tyr Lys Leu Pro Asp Leu Cys
            290                 295                 300

Thr Glu Leu Asn Thr Ser Leu Gln Asp Ile Glu Ile Thr Cys Val Tyr
305                 310                 315                 320

Cys Lys Thr Val Leu Glu Leu Thr Glu Val Phe Glu Phe Ala Phe Lys
                325                 330                 335

Asp Leu Phe Val Val Tyr Arg Asp Ser Ile Pro His Ala Ala Cys His
            340                 345                 350

Lys Cys Ile Asp Phe Tyr Ser Arg Ile Arg Glu Leu Arg Tyr Tyr Ser
            355                 360                 365

Asp Ser Val Met Tyr Gly Pro Lys Ala Thr Leu Gln Asp Ile Val Leu
            370                 375                 380

His Leu Glu Pro Gln Asn Glu Ile Pro Val Asp Leu Leu Cys His Glu
385                 390                 395                 400

Gln Leu Ser Asp Ser Glu Glu Glu Asn Asp Glu Ile Asp Gly Val Asn
            405                 410                 415

His Gln His Leu Pro Ala Arg Arg Ala Glu Pro Gln Arg His Thr Met
            420                 425                 430

Leu Cys Met Cys Phe Tyr Ser Arg Ile Arg Glu Leu Arg Tyr Tyr Ser
            435                 440                 445

Asp Ser Val Tyr Gly Asp Thr Leu Glu Lys Leu Thr Asn Thr Gly Leu
450                 455                 460
```

-continued

```
Tyr Asn Leu Leu Ile Arg Cys Leu Arg Cys Gln Lys Pro Leu Asn Pro
465                 470                 475                 480

Ala Glu Lys Leu Arg His Leu Asn Glu Lys Arg Arg Phe His Lys Ile
                485                 490                 495

Ala Gly His Tyr Arg Gly Gln Cys His Ser Cys Cys Asn Arg Ala Arg
            500                 505                 510

Gln Glu Arg Leu Gln Arg Arg Glu Thr Gln Val Ala Arg Arg Ala
        515                 520                 525

Glu Pro Gln Arg His Thr Met Leu Cys Met Cys Cys Lys Cys Glu Ala
    530                 535                 540

Arg Ile Glu Leu Val Glu Ser Ser Ala Asp Asp Leu Arg Ala Phe
545                 550                 555                 560

Gln Gln Leu Phe Leu Ser Thr Leu Ser Phe Val Cys Pro Trp Cys Ala
                565                 570                 575

Ser Gln Gln

<210> SEQ ID NO 2
<211> LENGTH: 23
<212> TYPE: PRT
<213> ORGANISM: Homo sapiens

<400> SEQUENCE: 2

Met Asp Ala Met Lys Arg Gly Leu Cys Cys Val Leu Leu Leu Cys Gly
1               5                   10                  15

Ala Val Phe Val Ser Pro Ser
            20

<210> SEQ ID NO 3
<211> LENGTH: 163
<212> TYPE: PRT
<213> ORGANISM: Homo sapiens

<400> SEQUENCE: 3

Ile Thr Gln Asp Cys Ser Phe Gln His Ser Pro Ile Ser Ser Asp Phe
1               5                   10                  15

Ala Val Lys Ile Arg Glu Leu Ser Asp Tyr Leu Leu Gln Asp Tyr Pro
                20                  25                  30

Val Thr Val Ala Ser Asn Leu Gln Asp Glu Glu Leu Cys Gly Gly Leu
            35                  40                  45

Trp Arg Leu Val Leu Ala Gln Arg Trp Met Glu Arg Leu Lys Thr Val
        50                  55                  60

Ala Gly Ser Lys Met Gln Gly Leu Leu Glu Arg Val Asn Thr Glu Ile
65                  70                  75                  80

His Phe Val Thr Lys Cys Ala Phe Gln Pro Pro Pro Ser Cys Leu Arg
                85                  90                  95

Phe Val Gln Thr Asn Ile Ser Arg Leu Leu Gln Glu Thr Ser Glu Gln
                100                 105                 110

Leu Val Ala Leu Lys Pro Trp Ile Thr Arg Gln Asn Phe Ser Arg Cys
            115                 120                 125

Leu Glu Leu Gln Cys Gln Pro Asp Ser Ser Thr Leu Pro Pro Pro Trp
        130                 135                 140

Ser Pro Arg Pro Leu Glu Ala Thr Ala Pro Thr Ala Pro Gly Gly Gly
145                 150                 155                 160

Ser Gly Asp
```

<210> SEQ ID NO 4
<211> LENGTH: 1746
<212> TYPE: DNA
<213> ORGANISM: Artificial Sequence
<220> FEATURE:
<223> OTHER INFORMATION: Codon-optimized nucleotide sequence of
      structurally modified E6 and E7 derived from HPV16 and HPV18

<400> SEQUENCE: 4

```
atgcaccaga gagaaccgc catgttccag gaccctcagg agagacctag gaagctgcct      60
cacctgtgta cagagctcca gacaaccatc cacgacatca tcctggagtg cgtgtactgt     120
aagcagcagc tgctgagaag agaggtgtac gacttcgcct tcagagacct gtgcatcgtg     180
tacagagacg caaccctta cgccgtgtgc gataagtgtc tgaagttcta ttccaaaatc     240
tccgaatata ggtacatgca cggcgacacc cctaccctgc acgagtacat gctggacctc     300
cagcctgaga ccacagacct gtactgctac gagcagctga cgacagctc tgaggaagag     360 gacgagattg acggacctgc tggccaggcc gagcctgaca gagcccacta caatatcgtg     420
acattctgtt gcaaatgcga ctccacactg gacaagtgcc tgaagttcta cagcaagatc     480
tctgagtaca gatactactg ctactctgtg tacggcacca cactggagca gcagtacaac     540
aagcctctgt gcgacctcct gatccgctgc atcaactgcc agaagcctct gtgccctgag     600
gagaagcaga gacacctgga caagaagcag cggttccaca acatcagagg cagatggacc     660
ggcaggtgca tgtcctgctg tagatcctcc agaaccagac gggagaccca gctgcactac     720
aacatcgtga ccttctgctg caagtgcgac tctaccctga actgtgcgt gcagtctacc     780 cacgtggaca tcagaaccct ggaggacctg ctgatgggca ccctgggcat cgtgtgccct     840
atctgctctc agaagcctat ggccaggttc gaggaccta ccagaagacc ctacaagctg     900
cctgacctgt gcaccgagct gaacacctct ctgcaagaca tcgagatcac ctgcgtgtac     960
tgcaagaccg tgctggagct gaccgaggtg ttcgagttcg ccttcaagga cctgttcgtg    1020
gtgtacagag acagcatccc tcacgctgcc tgccacaagt gcatcgactt ctattccagg    1080
atcagggagc tgcgctatta ctccgactct gtgatgtacg gccccaaggc cacctccag    1140 gacatcgtgc tgcacctgga gcctcagaac gagatccccg tggacctgct gtgccacgag    1200
cagctgtctg actctgaaga ggagaacgac gagatcgacg gcgtgaacca ccagcacctg    1260
cctgccagga gagctgaacc cagcggcat accatgctgt gtatgtgctt ctactctagg    1320
atcagagagc tgaggtacta ctctgactct gtgtacggcg acccctgga gaagctgacc    1380 aacaccggcc tgtacaacct gctgatccgg tgcctgaggt gccagaagcc tctgaaccct    1440
gccgagaagc tgagacacct gaacgagaag agaagattcc acaagatcgc tggccactac    1500
agaggccagt gccactcttg ctgcaacaga gccgacagg agagactcca gcggagaagg    1560
gagacccagg tggccagaag agccgagcct cagagacaca ccatgctgtg catgtgctgc    1620
aagtgcgagg ccagaatcga gctggtggtg gagagctctg ccgacgacct gagagccttc    1680
cagcagctgt tcctgtctac cctgagcttc gtgtgcccct tggtgcgcct tcagcagtaa    1740
tctaga                                                                1746
```

<210> SEQ ID NO 5
<211> LENGTH: 69
<212> TYPE: DNA
<213> ORGANISM: Artificial Sequence
<220> FEATURE:
<223> OTHER INFORMATION: Codon-optimized tissue plasminogen activator
      secretory signal sequence nucleotide sequence

```
<400> SEQUENCE: 5
atggatgcta tgaaacgggg cctgtgctgc gtgctgctcc tgtgcggcgc tgtgtttgtg    60
agccctagc                                                           69

<210> SEQ ID NO 6
<211> LENGTH: 489
<212> TYPE: DNA
<213> ORGANISM: Artificial Sequence
<220> FEATURE:
<223> OTHER INFORMATION: Codon-optimized fms-like tyrosine kinase 3
      ligand nucleotide sequence

<400> SEQUENCE: 6
atcacccagg actgctcctt ccaacacagc cccatctcct ccgacttcgc tgtcaaaatc    60
cgtgagctgt ctgactacct gcttcaagat tacccagtca ccgtggcctc caacctgcag   120
gacgaggagc tctgcggggg cctctggcgg ctggtcctgg cacagcgctg gatggagcgg   180
ctcaagactg tcgctgggtc caagatgcaa ggcttgctgg agcgcgtgaa cacggagata   240
cactttgtca ccaaatgtgc ctttcagccc cccccagct gtcttcgctt cgtccagacc    300
aacatctccc gcctcctgca ggagacctcc gagcagctgg tggcgctgaa gccctggatc   360
actcgccaga acttctcccg gtgcctggag ctgcagtgtc agcccgactc ctcaaccctg   420
ccacccccat ggagtccccg gcccctggag gccacagccc cgacagcccc gggcggcggc   480
agcggcgat                                                          489
```

COMPOSITION FOR PREVENTING OR TREATING CERVICAL CANCER HAVING HUMAN PAPILLOMAVIRUS PLASMODIUM AND IMMUNITY ENHANCER

RELATED APPLICATIONS

This application is a 35 U.S.C. §371 national phase application of PCT/KR2010/005367 (WO 2012/020871), filed on Aug. 13, 2010, entitled "Composition for Preventing or Treating Cervical Cancer Having Human Papillomavirus Plasmodium and Immunity Enhancer", which is incorporated herein by reference in its entirety.

BACKGROUND

1. Field of the Invention

The present invention relates to a composition for preventing or treating cervical cancer comprising a human papillomavirus (HPV) plasmodium and an immunity enhancer, and, more particularly, to a fusion protein including a fusion polypeptide recombined to transform a 3-dimensional (3D) structure of E6 and E7, which are antigens of types 16 and 18 HPV, a signal peptide for secreting the fusion polypeptide outside the cells, and an immunity enhancer peptide present in an individual, wherein the fusion protein may treat HPV-triggered tumors by inducing an immune response specific to HPV type 16 and 18 antigens.

Incorporated by reference herein in its entirety is the Sequence Listing entitled "PCT_KR2010_005367_Sequence Listing_ST25-2," created Apr. 4, 2014, size of 11 kilobytes.

2. Discussion of Related Art

Cervical cancer has been known as a disease that develops from infection of human papillomaviruses (HPVs) of very high concern such as types 16 and 18 (zur Hausen, H et al. *Biochem Biophys Acta* 1996, 1288; F55-F78, Mark H et al. *J Natl Cancer Inst* 1993, 85; 958-964). Among HPV proteins, E6 and E7 proteins play an important role in the onset of cervical cancer, and are important target substances used to prepare a vaccine for treating and preventing cervical cancer since they are confirmed to be expressed in 99% of tumor tissues from cervical cancer patients (von Knebel Doeberitz et al. *Int. J. Cancer* 1992, 51; 831-834). In this case, E6 is bound to p53 known as a tumor suppressor protein to facilitate degradation of the p53, thereby obstructing a cell cycle from leading to the apoptosis pathway, and E7 is bound to a retinoblastoma protein, pRb, known as a tumor suppressor factor to inactivate the retinoblastoma protein and facilitate degradation of the retinoblastoma protein, thereby allowing the cell cycle to enter the S stage (Cobrinik et al., *Trends Biochem Sci* 1992, 17:312-5).

In clinical trials using a composition including a nucleic acid sequence in which HPV16 E6 and E7 proteins are simultaneously expressed to treat cervical cancer, however, the composition has shown a poor therapeutic effect (Garcia F et al. *Obstet Gynecol* 2004, 103; 317-326). These results indicate that a sufficient antigen-specific immune response to treat or suppress cervical cancer is not triggered when only an HPV antigen is simply administered.

Therefore, it is necessary to enhance the immunogenicity of E6 and E7 proteins to treat cervical cancer, and remove the proteins' capability of developing into cancer.

SUMMARY OF THE INVENTION

The present invention is directed to providing a novel fusion protein for preventing or treating HPV-triggered diseases, and a polynucleotide encoding the fusion protein. Here, the fusion protein suppresses the HPV E6 and E7 proteins' capability of developing into cancer and shows enhanced immunogenicity as well.

Also, the present invention is directed to providing a recombinant vector expressing the fusion protein, a host cell including the recombinant vector, and a method of expressing the fusion protein using the host cell.

In addition, the present invention is directed to providing a composition for preventing or treating HPV-triggered diseases using the fusion protein.

Furthermore, the present invention is directed to providing a method of preventing or treating HPV-triggered diseases using the composition.

One aspect of the present invention provides a fusion protein including a fusion polypeptide configured to transform a 3D structure of E6 and E7 derived from HPV types 16 and 18 and having an amino acid sequence set forth in SEQ ID NO: 1, a signal peptide for secreting the fusion polypeptide, and an immunity enhancer peptide.

Another aspect of the present invention provides a polynucleotide encoding the fusion protein according to one exemplary embodiment of the present invention.

Still another aspect of the present invention provides a recombinant vector including the polynucleotide according to one exemplary embodiment of the present invention.

Still another aspect of the present invention provides a host cell transformed with the recombinant vector according to one exemplary embodiment of the present invention.

Still another aspect of the present invention provides a method of expressing the fusion protein of the present invention by incubating the host cell transformed with the recombinant vector according to one exemplary embodiment of the present invention.

Still another aspect of the present invention provides a composition for preventing or treating an HPV-triggered disease in an individual in need thereof. Here, the composition includes at least one selected from the group consisting of the fusion protein according to one exemplary embodiment of the present invention, the host cell transformed with the recombinant vector that expresses the fusion protein, and a homogenate of the host cell as an effective ingredient.

Yet another aspect of the present invention provides a method of preventing or treating HPV-triggered diseases in an individual in need thereof. Here, the method includes administering an effective amount of the composition according to one exemplary embodiment of the present invention to the individual.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which.

DETAILED DESCRIPTION OF EXEMPLARY EMBODIMENTS

Figure 1:
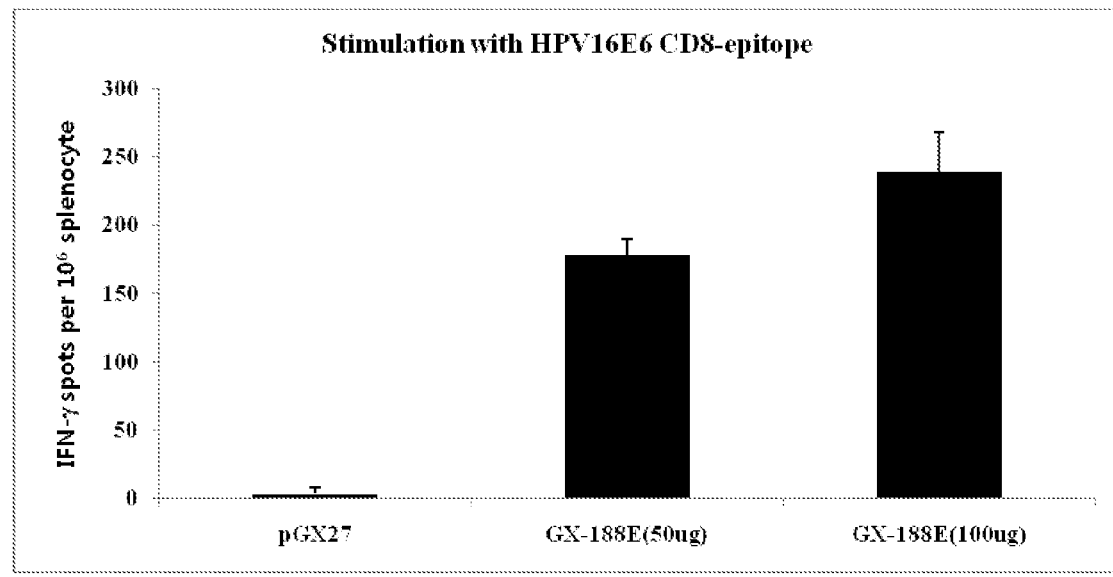
FIG. 1 is a graph showing the HPV16 E6-specific CD8+ T cellular responses which are induced by treatment with GX-188E according to one exemplary embodiment of the present invention after a tumor cell line, TC-1, is injected subcutaneously into C57BL/6 rats in a model of anticancer treatment.
Figure 2:
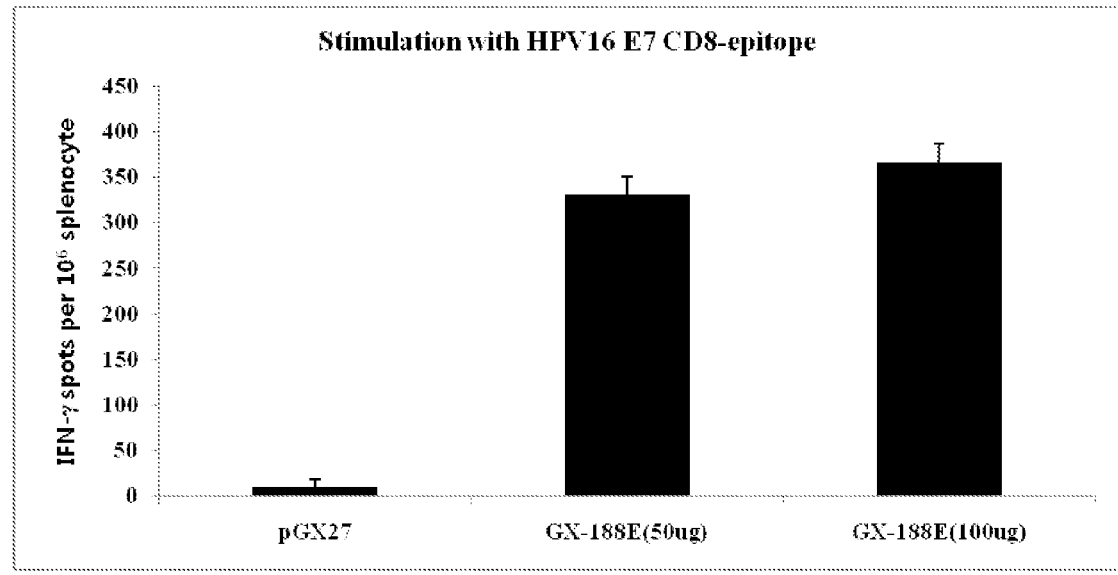
FIG. 2 is a graph showing the HPV16 E7-specific CD8+ T cellular responses which are induced by treatment with GX-188E according to one exemplary embodiment of the present invention after a tumor cell line, TC-1, is injected subcutaneously into C57BL/6 rats in the model of anticancer treatment.
Figure 3:
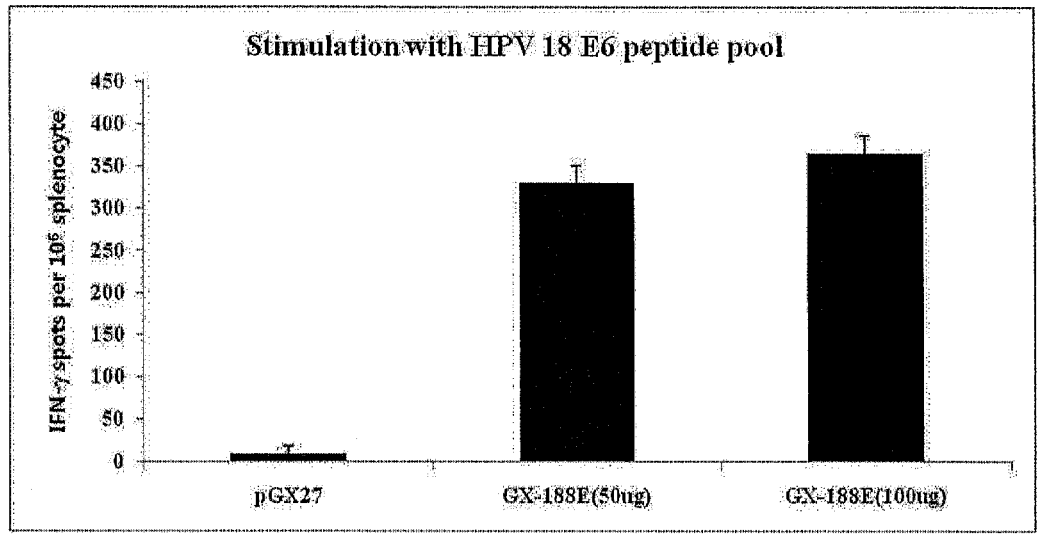
FIG. 3 is a graph showing the HPV18 E6-specific CD8+ T cellular responses which are induced by treatment with GX-188E according to one exemplary embodiment of the present invention after a tumor cell line, TC-1, is injected subcutaneously into C57BL/6 rats in the model of anticancer treatment.
Figure 4:
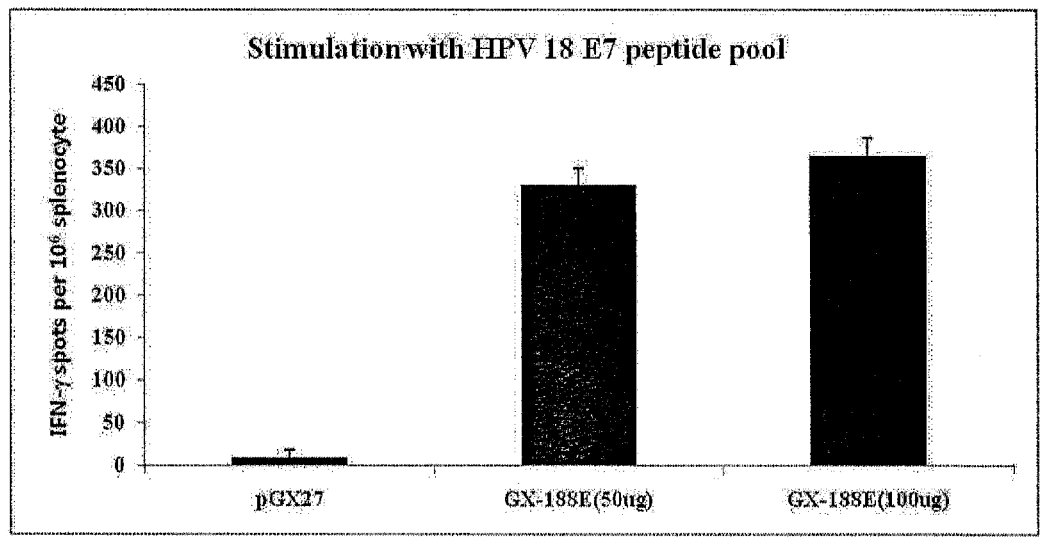
FIG. 4 is a graph showing the HPV18 E7-specific CD8+ T cellular response which is induced by treatment with GX-188E according to one exemplary embodiment of the present invention after a tumor cell line, TC-1, is injected subcutaneously into C57BL/6 rats in the model of anticancer treatment.

Hereinafter, exemplary embodiments of the present invention will be described in detail. However, the present invention is not limited to the embodiments disclosed below, but can be implemented in various forms. The following embodiments are described in order to enable those of ordinary skill in the art to embody and practice the present invention.

Although the terms first, second, etc. may be used to describe various elements, these elements are not limited by these terms. These terms are only used to distinguish one element from another. For example, a first element could be termed a second element, and, similarly, a second element could be termed a first element, without departing from the scope of exemplary embodiments. The term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The terminology used herein is for the purpose of describing particular embodiments only and is not intended to be limiting of exemplary embodiments. The singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, components and/or groups thereof, but do not preclude the presence or addition of one or more other features, integers, steps, operations, elements, components and/or groups thereof.

With reference to the appended drawings, exemplary embodiments of the present invention will be described in detail below. To aid in understanding the present invention, like numbers refer to like elements throughout the description of the figures, and the description of the same elements will be not reiterated.

Hereinafter, configurations of the present invention will be described in further detail.

The present invention is directed to providing a novel fusion protein including a fusion polypeptide configured to transform a 3D structure of E6 and E7 derived from HPV types 16 and 18 and having an amino acid sequence set forth in SEQ ID NO: 1, a signal peptide for secreting the fusion polypeptide, and an immunity enhancer peptide.

The fusion protein according to one exemplary embodiment of the present invention may include a fusion polypeptide recombined to transform a 3D structure of the E6 and E7 derived from the HPV types 16 and 18. More particularly, the fusion polypeptide is a fusion polypeptide in which $1^{st}$ to $85^{th}$ amino acids of the E6 protein derived from the HPV type 16, $1^{st}$ to $65^{th}$ amino acids of the E7 protein, $71^{st}$ to $158^{th}$ amino acids of the E6 protein, and $51^{st}$ to $98^{th}$ amino acids of the E7 protein, $1^{st}$ to $85^{th}$ amino acids of the E6 protein derived from the HPV type 18, $1^{st}$ to $65^{th}$ amino acids of the E7 protein, $71^{st}$ to $158^{th}$ amino acids of the E6 protein, and $51^{st}$ to $105^{th}$ amino acids of the E7 protein are bound in sequence.

Most particularly, the fusion polypeptide may have an amino acid sequence set forth in SEQ ID NO: 1.

Also, the signal peptide refers to a peptide including approximately 20 to 30 amino acids, which serves to secrete a protein expressed in cells, particularly, a protein including a fusion polypeptide of E6 and E7 outside the cells. Also, a nucleic acid sequence encoding the signal peptide is referred to as a "secretory signal sequence." The fusion polypeptide of E6 and E7 according to one exemplary embodiment of the present invention is a protein (i.e., a nucleus protein) expressed in the nuclei of the cells infected with viruses, and thus shows weak immunity. Therefore, the signal peptide expressed from the secretory signal sequence induces secretion of E6 and E7 antigens whose 3D structure is transformed outside the cells, which leads to an increase in antigen-specific humoral and cellular immune responses.

A signal peptide used in higher eukaryotic cells may be used as the signal peptide. For example, a secretory signal sequence of tissue plasminogen activator (tPa), HSV gDs or a growth hormone may be used. More preferably, a tPa may be used. Most preferably, the signal peptide has an amino acid sequence set forth in SEQ ID NO: 2.

Also, the immunity enhancer peptide refers to a peptide that serves to enhance an immune response by activating cells associated with the immune response (for example, dendritic cells, etc.).

A CD40 ligand, an fms-like tyrosine kinase-3 (Flt3) ligand, flagellin, or OX40 may be used as the immunity enhancer peptide. More preferably, the Flt3 ligand may be used herein. The Flt3 ligand is a factor for inducing proliferation and maturation of dendritic cells (DCs), which may enhance an immune response against an antigen and show an excellent effect to relieve a tumor when fused with a tumor antigen. Most preferably, the Flt3 ligand may have an amino acid sequence set forth in SEQ ID NO: 3.

Also, the present invention is directed to providing a polynucleotide encoding the fusion protein according to one exemplary embodiment of the present invention.

The polynucleotide encodes the fusion protein according to one exemplary embodiment of the present invention. Here, the fusion polypeptide of E6 and E7 may be encoded from a base sequence set forth in SEQ ID NO: 4, but the present invention is not limited thereto. Also, the signal peptide may be encoded from a base sequence set forth in SEQ ID NO: 5, but the present invention is not limited thereto. The immunity enhancer peptide may be encoded from a base sequence set forth in SEQ ID NO: 6, but the present invention is not limited thereto.

Also, the polynucleotide according to one exemplary embodiment of the present invention may be prepared using chemical synthesis or a genetic engineering technique. The chemical synthesis is known in the related art, and any method may be used herein. Also, the polynucleotide may be synthesized using commercially available nucleic acid synthesis and may be purchased from a nucleic acid supplier. When the polynucleotide is prepared using the genetic engineering technique, the polynucleotide may be prepared, for example, by separately constructing nucleic acid fragments encoding a fusion polypeptide of E6 and E7, a signal peptide and an immunity enhancer peptide as known in the prior art and binding these fragments according to a frame thereof. A method of preparing the nucleic acid fragment is widely known in the related art. Therefore, a person having ordinary skill in the art may easily bind the nucleic acid fragments using a proper restriction enzyme. According to a specific embodiment of the present invention, a method of preparing a polynucleotide using the chemical synthesis is disclosed.

In addition, the present invention is directed to providing a recombinant vector including the polynucleotide according to one exemplary embodiment of the present invention.

In the present invention, the term "vector" refers to a gene construct including an exogenous DNA fragment which is inserted into the genome to encode a polypeptide. A vector associated with the present invention is a vector in which a secretory signal sequence, a nucleic acid sequence encoding a fusion polypeptide of E6 and E7 whose HPV 3D structure is transformed, and a nucleic acid sequence encoding the immunity enhancer peptide are inserted into the genome. Examples of the vector may include a plasmid vector, a cosmid vector, a bacteriophage vector, a yeast vector, or a viral vector such as an adenoviral vector, a retroviral vector or an adeno-associated viral vector.

The secretory signal sequence is a nucleic acid sequence encoding a peptide that can secrete a tumor antigen expressed in the cells outside the cells to recognize immunocytes. For example, the secretory signal sequence may include a secretory signal sequence of tPa, HSV gDs, or a growth hormone. Preferably, a secretory signal sequence used in higher eukaryotic cells including a mammal, and, more preferably, the tPa may be used herein. Most preferably, the secretory signal sequence may have a base sequence set forth in SEQ ID NO: 5. Also, the secretory signal sequence according to one exemplary embodiment of the present invention may be substituted with a codon having a high expression frequency, and used in a host cell.

Also, the nucleic acid sequence encoding the immunity enhancer peptide refers to a nucleic acid sequence encoding a peptide that enhances an immune response by activating cells associated with the immune response (for example, dendritic cells, etc.). A CD40 ligand, an Flt3 ligand, flagellin, or OX40 may be used as the immunity enhancer peptide. More preferably, the Flt3 ligand may be used as the immunity enhancer peptide. Also, the nucleic acid sequence encoding the immunity enhancer peptide according to one exemplary embodiment of the present invention may be substituted with a codon having a high expression frequency, and used in a host cell.

In addition, the polynucleotide included in the recombinant vector according to one exemplary embodiment of the present invention may be substituted with a codon having a high expression frequency in the host cell. Among codons commanding amino acids when DNA is transcribed and translated into a protein in a host cell, there are codons having high preference, depending on the host. As used in the present invention, the term "being substituted with a codon having a high expression frequency in a host cell" or "codon-optimized" refers to a state in which a polynucleotide is substituted with theses codons having high preference to increase the expression efficiency of amino acids or a protein encoded by nucleic acids of the polynucleotide.

Here, the "host cell" includes a prokaryotic or eukaryotic cell. In this case, the eukaryotic cell includes a lower eukaryotic cell including those of fungi or yeast, as well as a higher eukaryotic cell including those of mammals.

The recombinant vector according to one exemplary embodiment of the present invention may include a nucleic acid sequence encoding the fusion protein in a suitable form to express the nucleic acid sequence encoding the fusion protein of the present invention in a host cell. That is, the recombinant vector according to one exemplary embodiment of the present invention includes one or more regulatory sequences selected based on a host cell that may be used for expression. Here, the regulatory sequences may be operably coupled to a nucleic acid sequence to be expressed.

The term "being operably coupled" refers to a state in which a desired nucleotide sequence (for example, in an in vitro transcription/translation system or a host cell) is coupled to the regulatory sequence in a suitable manner to express the desired nucleotide sequence.

The term "regulatory sequence" refers to a sequence including a promoter, an enhancer and another regulatory element (for example, a polyadenylation signal). The regulatory sequence includes a sequence commanding constitutive expression of a desired nucleic acid sequence in many host cells, and a sequence commanding expression of a desired nucleic acid sequence only in a certain host cell (for example, a tissue-specific regulatory sequence). A person having ordinary skill in the art may understand that the design of an expression vector may vary according to factors such as selection of a host cell to be transformed, and a level of expression of a desired protein. The expression vector according to one exemplary embodiment of the present invention may be introduced into a host cell to express the fusion protein.

Also, the expression vector according to one exemplary embodiment of the present invention may be, for example, prepared using the standard recombinant DNA technology. For example, the standard recombinant DNA technology includes ligation of blunt and cohesive termini, treatment with a restriction enzyme to provide a proper terminus, removal of a phosphate group through treatment with alkaline phosphatase to prevent inappropriate binding, and enzymatic binding using T4 DNA ligase. The expression vector according to one exemplary embodiment of the present invention may be prepared by recombining DNA encoding a signal peptide obtained by chemical synthesis or genetic recombination technology, DNA encoding a fusion polypeptide of HPV E6 and E7, and DNA encoding an immunity enhancer peptide with a vector including a proper regulatory sequence. The vector including the regulatory sequence may be purchased or prepared in a commercially available fashion. In the present invention, a vector for preparing a DNA vaccine, that is, pGX27, was prepared for use.

According to one exemplary embodiment, the recombinant vector of the present invention may be used to prepare a cell line for producing the fusion protein according to one exemplary embodiment of the present invention, or may be used as a vector for transferring a gene in gene therapy, or a pharmaceutically active ingredient which itself is administered to an individual.

Also, the present invention is directed to providing a host cell transformed with the recombinant vector according to one exemplary embodiment of the present invention.

The kind of the host cell is as listed above.

The transformation may be performed using a known method of introducing a nucleic acid sequence into an organism, a cell, a tissue or an organ. In this case, a method that may be used may be selected so that it can be suitable for a host cell within the scope of the present invention to be understood at a level of a person having ordinary skill in the art. For example, such a method includes electroporation, protoplast fusion, calcium phosphate (CaPO$_4$) precipitation, calcium chloride (CaCl$_2$) precipitation, agitation using a silicon carbide fiber, agrobacteria-mediated transformation, PEG, dextran sulfate, and lifofectamin, but the present invention is not limited thereto.

Also, the present invention is directed to providing a method of expressing a fusion protein according to one exemplary embodiment of the present invention by incubating the transformed host cell according to one exemplary embodiment of the present invention.

The fusion protein according to one exemplary embodiment of the present invention may be easily expressed and mass-produced by incubating the transformed host cell in a proper medium, or introducing the transformed host cell into any animal and incubating the transformed host cell in vivo.

In addition, the present invention is directed to providing a composition for preventing or treating an HPV-triggered disease in an individual in need thereof. Here, the composition includes at least one selected from the group consisting of the fusion protein according to one exemplary embodiment of the present invention, a host cell transformed with a recombinant vector expressing the fusion protein, and a homogenate of the fusion protein as an effective ingredient.

In the present invention, the term "individual" includes a mammal such as a human, a monkey, a rat, a pig, a bovine and a rabbit, but the present invention is not limited thereto.

Also, the HPV-triggered disease may include cervical cancer, anogenital warts, verruca, etc.

In addition, the composition according to one exemplary embodiment of the present invention may further include a pharmaceutically allowable carriers. Here, the pharmaceutically allowable carriers includes lactose, glucose, saccharose, sorbitol, mannitol, starch, gum acacia, alginate, gelatine, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate and mineral oil. Also, the composition may further include a lubricant, a wetting agent, a flavoring agent, an emulsifying agent and a preservative.

For example, the composition according to one exemplary embodiment of the present invention may be directly administered to an individual using a route of administration such as intravenous, intramuscular, oral, transdermal, intramucosal, intranasal, intratracheal or subcutaneous administration, but the present invention is not limited thereto. The composition according to one exemplary embodiment of the present invention may be administered indirectly to an individual by administering the composition into in vitro incubated cells and administering the incubated cells to the individual. In this case, the composition according to one exemplary embodiment of the present invention may be administered systemically or locally.

The composition according to one exemplary embodiment of the present invention may be formulated into an oral preparation such as a granule, a powder, a solution, a tablet, a capsule or a dry syrup, or a parenteral formulation such as an injectable solution, but the present invention is not limited thereto. Preferably, the composition according to one exemplary embodiment of the present invention may be prepared in the form of a solution or an injectable solution.

As the active ingredient, the fusion protein or the recombinant expression vector according to one exemplary embodiment of the present invention may be administered at an effective amount of approximately 0.05 to 500 mg/kg, preferably 0.5 to 50 mg/kg. In this case, the administration may be performed in consideration of a single dose or divided doses. However, an amount of the active ingredient to be administered may be determined in consideration of various factors such as the conditions to be treated, the age and body weight of a patient, and the severity of the conditions, but the present invention is not limited thereto.

Furthermore, the present invention is directed to providing a method of preventing or treating an HPV-triggered disease in an individual in need thereof. Here, the method includes administering an effective amount of the composition of the present invention to the individual.

A pharmaceutical composition according to one exemplary embodiment of the present invention, use thereof, a method of administering the same, and a dose of the pharmaceutical composition are as described above.

In the method according to one exemplary embodiment of the present invention, the individual includes a mammal such as a human, a monkey, a rat, a pig, a bovine and a rabbit, but the present invention is not limited thereto.

Also, the HPV-triggered disease may include cervical cancer, anogenital warts, verruca, etc.

Hereinafter, the present invention will be described in further detail with reference to Examples according to the present invention and Comparative Examples which do not fall within the scope of the present invention. However, it should be understood that the Examples are not intended to limit the scope of the present invention.

Example 1

Construction of GX-188E DNA

Abbreviations used in the Examples of the present invention are defined as follows. An optimized nucleic acid sequence, "tPa" or "t" refers to a secretory signal sequence of a tissue plasminogen activator, and "F" or "Flt3L" refers to an fms-like tyrosine kinase-3 ligand.

A codon-optimized tPa secretory signal sequence having a nucleic acid sequence set forth in SEQ ID NO: 5 and a codon-optimized Flt3L having a nucleic acid sequence set forth in SEQ ID NO: 6 were chemically synthesized while the codon-optimized tPa and Flt3L secretory signal sequences were coupled to each other. A terminus of the synthesized signal sequence was provided with KpnI (5') and NheI (3') restriction sites to facilitate insertion into a vector. A vector for preparing a DNA vaccine, that is, pGX10 (Korean Patent Publication No. 2003-0047667) was digested with KpnI and NheI restriction enzymes, and then ligated with the synthesized tPa-Flt3L signal sequence using ligase to prepare a pGX10/tF vector.

A codon-optimized nucleic acid sequence coding for $1^{st}$ to $85^{th}$ amino acids of the HPV16 E6, a codon-optimized nucleic acid sequence coding for $1^{st}$ to $65^{th}$ amino acids of the HPV16 E7, a codon-optimized nucleic acid sequence coding for $71^{st}$ to $158^{th}$ amino acids of the HPV16 E6, a codon-optimized nucleic acid sequence coding for $51^{st}$ to $98^{th}$ amino acids of the HPV16 E7, a codon-optimized nucleic acid sequence coding for $1^{st}$ to $85^{th}$ amino acids of the HPV18 E6, a codon-optimized nucleic acid sequence coding for $1^{st}$ to $65^{th}$ amino acids of the HPV18 E7, a codon-optimized nucleic acid sequence coding for $71^{st}$ to $158^{th}$ amino acids of the HPV18 E6, and a codon-optimized nucleic acid sequence coding for $51^{st}$ to $105^{th}$ amino acids of the HPV 18 E7 were chemically synthesized while the codon-optimized nucleic acid sequences were coupled to one another (hereinafter referred to as 16E6N16E7N16E6C16E7C18E6N18E7N18E6C18E7C:

SEQ ID NO: 4). A terminus of the synthesized signal sequence was provided with NheI (5') and XbaI (3') restriction sites to facilitate insertion into a vector. The pGX10/tF vector was digested with NheI and XbaI restriction enzymes, and then ligated with the synthesized signal sequence, 16E6N16E7N16E6C16E7C18E6N18E6N18E7C, using ligase to construct a pGX10/tF16E6N16E7N16E6C16E7C18E6N18E7N18E6C18E7C vector. Then, the pGX10/tF16E6N16E7N16E7C18E6N18E7N18E6C18E7C vector was digested with KpnI and XbaI restriction enzymes to separate tF16E6N16E7N16E6C16E7C18E6N18E7N18E6C18E7C, and pGX10 was digested with KpnI and XbaI restriction enzymes, and then ligated with tF16E6N16E7N16E6C16E7C18E6N18E7N18E6C18E7C using ligase to construct a pGX27/tF16E6N16E7N16E6C16E7C18E6N18E7N18E6C18E7C vector (hereinafter referred to as "GX-188E").

Example 2

Confirmation of Therapeutic Effect of GX-188E on Cervical Cancer

To confirm a therapeutic effect of GX-188E on cervical cancer, TC-1 tumor cells were subcutaneously injected into C57BL/6 rats at a concentration of $5 \times 10^5$ cells, and GX-188E was intramuscularly injected at doses of 50 μg and 100 μg on days 3 and 8, followed by performing electroporation. A change in volume of tumor cells was observed from the day of injection to day 27, and the spleens of the rats were extracted on Day 36. Then, $1 \times 10^6$ cells were put into a plate coated with 50 μl of a 5 μg/ml anti-mouse IFN-g antibody (BD Pharmigen, San Diego, Calif.) together with IL-2 and an HPV16 E6 CD8 T cell epitope ($E6_{48-57}$; EVYDFAFRDL, Peptron, Korea), an HPV18 E7 CD8 T cell epitope ($E7_{49-57}$; RAHYNIVTF, Peptron, Korea), an HPV18 E6 peptide pool, or an HPV18 E7 peptide pool, and incubated at 37° C. for 24 hours in a 5% $CO_2$ incubator (Froma, Minn., USA). The plate was washed with PBST, and a 2 μg/ml IFN-g detection antibody conjugated with biotin (BD Pharmigen, San Diego, Calif.) was put into the plate at a dose of 50 μl, and incubated at room temperature for approximately 3 hours. Subsequently, the plate was washed with PBST, and streptavidin-alkaline phosphate (AKP) diluted at 1:2000 was put into the plate at a dose of 50 μA and incubated at room temperature for 1 hour. Then, the plate was washed with PBST, and 66 μl of NBT (Promega, Madison, Wis.) and 33 μl of BCIP (Promega, Madison, Wis.) were added based on 10 ml of an alkaline phosphate buffer. Thereafter, 50 μl of the resulting solution was added and reacted. The plate was put into a 37° C. incubator and kept for approximately 30 minutes to facilitate a color reaction. Then, the plate was washed with distilled water (D.W.), and colored spots were counted using a reader.

The T cell immune responses specific to HPV16 E6 and E7, and HPV18 E6 and E7 were measured in the HPV16 E6 CD8 T cell epitope, the HPV16 E7 CD8 T cell epitope, the HPV18 E6 peptide pool and the HPV18 E7 peptide pool using an enzyme-linked immunosorbent spot (ELISPOT) assay. As a result, it was confirmed that the GX-188E induced a strong antigen-specific immune response, and simultaneously induced an immune response specific to the E6 and E7 of the HPV16 and HPV18 (see FIGS. 1, 2, 3 and 4).

Figure 5:
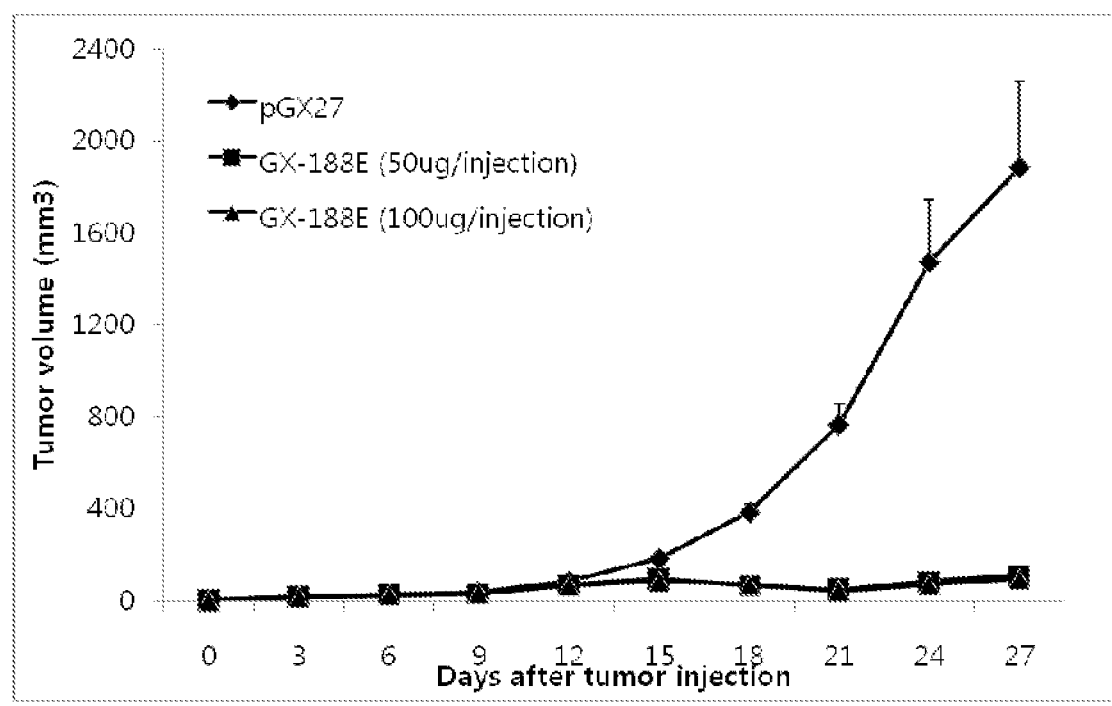
FIG. 5 is a graph showing the anti-cancer effects which are caused by treatment with GX-188E according to one exemplary embodiment of the present invention after a tumor cell line, TC-1, is injected subcutaneously into C57BL/6 rats in the model of anticancer treatment.

Also, it was confirmed that a volume of tumor was significantly reduced in the rats whose TC-1 tumor cells were immunologically treated with the GX-188E, compared with the rats injected with the pGX27 (control) (see FIG. 5).

INDUSTRIAL APPLICABILITY

The fusion protein according to the present invention can be used as a therapeutic agent for treating HPV-triggered tumors.

The fusion protein according to the present invention, which is prepared to include a fusion polypeptide recombined to transform a 3D structure of E6 and E7 proteins derived from the HPV types 16 and 18, a signal peptide for secreting the fusion polypeptide outside the cells, and an immunity enhancer peptide present in an individual, can treat the HPV-triggered tumors by inducing a strong immune response specific to the antigens against the HPV types 16 and 18.

While the invention has been shown and described with reference to certain exemplary embodiments thereof, it will be understood by those skilled in the art that various changes in form and details may be made therein without departing from the scope of the invention as defined by the appended claims.

What is claimed is:

1. A polynucleotide encoding a fusion protein comprising the sequence of SEQ ID NO:1.

2. The polynucleotide of claim 1, further comprising a nucleic acid sequence encoding an immunity enhancer peptide.

3. The polynucleotide of claim 2, wherein the immunity enhancer peptide is selected from a CD40 ligand, an fms-like tyrosine kinase-3 (Flt3) ligand, a flagellin, and an OX40.

4. The polynucleotide of claim 2, wherein the immunity enhancer peptide comprises the sequence of SEQ ID NO: 3.

5. The polynucleotide of claim 1, further comprising a nucleic acid sequence encoding a signal peptide.

6. The polynucleotide of claim 5, wherein the signal peptide is selected from a tissue plasminogen activator ("tPa") signal peptide, a Herpes Simplex Virus glycoprotein Ds ("HSV gDs") signal peptide, and a growth hormone signal peptide.

7. The polynucleotide of claim 5, wherein the signal peptide comprises the sequence of SEQ ID NO: 2.

8. The polynucleotide of claim 1, which is codon optimized.

9. The polynucleotide of claim 8, comprising the sequence of SEQ ID NO: 4.

10. The polynucleotide of claim 2, wherein the nucleic acid sequence encoding the immunity enhancer peptide is codon optimized.

11. The polynucleotide of claim 5, wherein the nucleic acid sequence encoding the signal peptide is codon optimized.

12. The polynucleotide of claim 11, which comprises the nucleotide sequences of SEQ ID NO: 4, SEQ ID NO: 5, and SEQ ID NO: 6.

13. A vector comprising the polynucleotide of claim 8.

14. A vector comprising the polynucleotide of claim 9.

15. The vector of claim 14, which is a plasmid.

16. A host cell comprising the vector of claim 13.

17. A composition comprising the polynucleotide of claim 1 and a pharmaceutically allowable carrier.

18. A composition comprising the polynucleotide of claim 9 and a pharmaceutically allowable carrier.

19. A composition comprising the vector of claim 15 and a pharmaceutically allowable carrier.

20. A fusion protein comprising an amino acid sequence, which is encoded by the polynucleotide of claim 1.

21. A fusion protein comprising an amino acid sequence, which is encoded by the polynucleotide of claim 2.

22. A method of expressing a fusion protein comprising transfecting the polynucleotide of claim 1 to a host cell under suitable condition.

23. A method of producing a fusion protein, comprising culturing the host cell of claim 16 under suitable conditions.

24. A method of inducing a T cell immune response to a subject in need thereof comprising administering the polynucleotide of claim 1 to the subject, wherein the T cell immune response is against an E6 protein of HPV serotype 16, an E7 protein of HPV serotype 16, an E6 protein of HPV serotype 18, and an E7 protein of HPV serotype 18.

25. A method of reducing the volume of a tumor triggered by HPV infection in a subject in need thereof comprising administering the polynucleotide of claim 1 to the subject, wherein the tumor volume is reduced after the administration.

* * * * *